United States Patent
Chowaniec et al.

(10) Patent No.: US 9,987,095 B2
(45) Date of Patent: Jun. 5, 2018

(54) ADAPTER ASSEMBLIES FOR INTERCONNECTING ELECTROMECHANICAL HANDLE ASSEMBLIES AND SURGICAL LOADING UNITS

(71) Applicant: Covidien LP, Mansfield, MA (US)

(72) Inventors: David Chowaniec, Rocky Hill, CT (US); Russell Pribanic, Roxbury, CT (US); Stanislaw Marczyk, Stratford, CT (US); Earl Zergiebel, Guilford, CT (US); Philip Irka, Northford, CT (US); Anand Subramanian, Stamford, CT (US); Paul Richard, Shelton, CT (US)

(73) Assignee: Covidien LP, Mansfield, MA (US)

( * ) Notice: Subject to any disclaimer, the term of this patent is extended or adjusted under 35 U.S.C. 154(b) by 538 days.

(21) Appl. No.: 14/672,731

(22) Filed: Mar. 30, 2015

(65) Prior Publication Data

US 2015/0374449 A1 Dec. 31, 2015

Related U.S. Application Data

(60) Provisional application No. 62/017,539, filed on Jun. 26, 2014.

(51) Int. Cl.
*A61B 17/068* (2006.01)
*A61B 90/00* (2016.01)
(Continued)

(52) U.S. Cl.
CPC ............ *A61B 90/06* (2016.02); *A61B 17/068* (2013.01); *A61B 17/07207* (2013.01);
(Continued)

(58) Field of Classification Search
CPC . A61B 90/06; A61B 2090/064; A61B 17/068; A61B 17/072; A61B 17/07207; A61B 2562/0261
See application file for complete search history.

(56) References Cited

U.S. PATENT DOCUMENTS

| 2,777,340 A | 1/1957 | Hettwer et al. |
| 2,957,353 A | 10/1960 | Babacz |

(Continued)

FOREIGN PATENT DOCUMENTS

| AU | 2008229795 A1 | 4/2009 |
| CA | 2451558 A1 | 1/2003 |

(Continued)

OTHER PUBLICATIONS

Extended European Search Report corresponding to International Application No. EP 15 15 1076.5 dated Apr. 22, 2015.

(Continued)

*Primary Examiner* — Stephen F Gerrity
*Assistant Examiner* — Joshua Kotis

(57) ABSTRACT

A force transmitting assembly of an adapter assembly includes a rotatable drive shaft, a strain sensor, and a drive member. The drive shaft includes a proximal portion, a distal portion, and a flange. The distal portion includes a threaded portion. The strain sensor is coupled to the drive shaft and disposed adjacent the flange such that longitudinal movement of the drive shaft imparts a force on the strain sensor via the flange. The distal drive member has a proximal end rotatably coupled to the threaded portion of the drive shaft and a distal end configured to be operatively coupled to a driven member of a surgical loading unit. Rotation of the drive shaft longitudinally moves the drive member relative to the drive shaft to actuate the surgical loading unit.

16 Claims, 8 Drawing Sheets

(51) Int. Cl.
  *A61B 17/072* (2006.01)
  *A61B 17/00* (2006.01)
  *A61B 17/29* (2006.01)
  *A61B 5/107* (2006.01)

(52) U.S. Cl.
  CPC ......... *A61B 5/1076* (2013.01); *A61B 17/2909* (2013.01); *A61B 2017/0046* (2013.01); *A61B 2017/00398* (2013.01); *A61B 2017/00473* (2013.01); *A61B 2017/00486* (2013.01); *A61B 2017/00862* (2013.01); *A61B 2017/2903* (2013.01); *A61B 2017/2925* (2013.01); *A61B 2090/064* (2016.02); *A61B 2562/0261* (2013.01)

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,869,719 A | 9/1989 | Hogan |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,647,526 A | 7/1997 | Green et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,968,012 A | 10/1999 | Ren et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,197,002 B1 | 3/2001 | Peterson |
| 6,221,023 B1 * | 4/2001 | Matsuba ............... A61B 5/0215 600/486 |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,692,482 B2 | 2/2004 | Heller et al. |
| 6,698,643 B2 | 3/2004 | Whitman |
| 6,699,177 B1 | 3/2004 | Wang et al. |
| 6,706,018 B2 | 3/2004 | Westlund et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,094,220 B2 | 8/2006 | Tanghoj et al. |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |

(56) References Cited

U.S. PATENT DOCUMENTS

| | | |
|---|---|---|
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,731,707 B2 | 6/2010 | Heller et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,798,999 B2 | 9/2010 | Bailey et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,854,727 B2 | 12/2010 | Belsley |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,988,699 B2 | 8/2011 | Martz et al. |
| 7,992,758 B2 | 8/2011 | Whitman et al. |
| 8,016,178 B2 | 9/2011 | Olson et al. |
| 8,016,752 B2 | 9/2011 | Armstrong et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,025,621 B2 | 9/2011 | Ewaschuk et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,292,963 B2 | 10/2012 | Miller et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,444,625 B2 | 5/2013 | Stalker et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2001/0034501 A1* | 10/2001 | Tom ............... A61B 17/3207 604/67 |
| 2002/0049454 A1 | 4/2002 | Whitman et al. |
| 2002/0128607 A1 | 9/2002 | Haury et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2004/0260246 A1 | 12/2004 | Desmond |
| 2005/0004553 A1 | 1/2005 | Douk |
| 2005/0075711 A1 | 4/2005 | Neary |
| 2005/0096507 A1 | 5/2005 | Prosek |
| 2005/0131390 A1* | 6/2005 | Heinrich ........... A61B 17/0469 606/1 |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0200185 A1 | 9/2006 | Marchek et al. |
| 2006/0229573 A1 | 10/2006 | Lamborne |

(56) References Cited

U.S. PATENT DOCUMENTS

| | | |
|---|---|---|
| 2006/0259073 A1 | 11/2006 | Miyamoto et al. |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0151390 A1* | 7/2007 | Blumenkranz ...... B25J 15/0009 74/490.06 |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0157092 A1* | 6/2009 | Blumenkranz ......... G01L 1/246 606/130 |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2009/0314821 A1 | 12/2009 | Racenet |
| 2010/0069942 A1 | 3/2010 | Shelton, IV |
| 2010/0174327 A1* | 7/2010 | Radermacher ....... A61B 17/155 606/86 R |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2010/0228233 A1 | 9/2010 | Kahn |
| 2010/0312257 A1* | 12/2010 | Aranyi ................. A61B 17/064 606/139 |
| 2011/0071508 A1 | 3/2011 | Duval et al. |
| 2011/0077673 A1 | 3/2011 | Grubac et al. |
| 2011/0118577 A1 | 5/2011 | Pfeiffer et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0184406 A1* | 7/2011 | Selkee ................. A61B 5/6885 606/41 |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0016402 A1 | 1/2012 | Weisshaupt et al. |
| 2012/0046577 A1* | 2/2012 | Soltz .................... A61B 17/068 600/587 |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116248 A1 | 5/2012 | McWeeney et al. |
| 2012/0116368 A1 | 5/2012 | Viola |
| 2012/0123389 A1 | 5/2012 | Shafran |
| 2012/0143002 A1 | 6/2012 | Aranyi et al. |
| 2012/0150063 A1 | 6/2012 | Rea |
| 2012/0172924 A1 | 7/2012 | Allen, IV |
| 2012/0223121 A1 | 9/2012 | Viola et al. |
| 2012/0245426 A1 | 9/2012 | Salvas et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323081 A1 | 12/2012 | Son |
| 2012/0323226 A1 | 12/2012 | Chowaniec et al. |
| 2012/0330285 A1 | 12/2012 | Hartoumbekis et al. |
| 2013/0012983 A1 | 1/2013 | Kleyman |
| 2013/0018361 A1 | 1/2013 | Bryant |
| 2013/0053782 A1 | 2/2013 | Shelton, IV |
| 2013/0090531 A1 | 4/2013 | Ryan |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0110085 A1 | 5/2013 | Adamson |
| 2013/0165942 A1 | 6/2013 | Tan-Malecki et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0220345 A1 | 8/2013 | Allphin et al. |
| 2013/0237950 A1 | 9/2013 | Gianotti et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0144970 A1 | 5/2014 | Aranyi et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0263561 A1* | 9/2014 | Castro ................. A61B 17/068 227/177.1 |
| 2014/0276932 A1 | 9/2014 | Williams et al. |
| 2014/0373652 A1 | 12/2014 | Zergiebel et al. |
| 2015/0157321 A1 | 6/2015 | Zergiebel et al. |
| 2015/0164502 A1 | 6/2015 | Richard et al. |
| 2015/0272577 A1 | 10/2015 | Lemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |

(56) References Cited

U.S. PATENT DOCUMENTS

| | | | |
|---|---|---|---|
| 2016/0106406 A1 | 4/2016 | Cabrera et al. | |
| 2016/0113648 A1 | 4/2016 | Zergiebel et al. | |
| 2016/0113649 A1 | 4/2016 | Zergiebel et al. | |

FOREIGN PATENT DOCUMENTS

| | | | |
|---|---|---|---|
| CN | 102247182 A | | 11/2011 |
| DE | 102008053842 A1 | | 5/2010 |
| EP | 0634144 A1 | | 1/1995 |
| EP | 0648476 A1 | | 4/1995 |
| EP | 0686374 A2 | | 12/1995 |
| EP | 0705571 A1 | | 4/1996 |
| EP | 1690502 A1 | | 8/2006 |
| EP | 1723913 A1 | | 11/2006 |
| EP | 1736112 A1 | | 12/2006 |
| EP | 1769754 A1 | | 4/2007 |
| EP | 1772105 A1 | | 4/2007 |
| EP | 1 813 203 A2 | | 8/2007 |
| EP | 1813199 A1 | | 8/2007 |
| EP | 1813211 A2 | | 8/2007 |
| EP | 1943954 A2 | | 7/2008 |
| EP | 1943956 A2 | | 7/2008 |
| EP | 1943958 A1 | | 7/2008 |
| EP | 1943976 A2 | | 7/2008 |
| EP | 1974676 A1 | | 10/2008 |
| EP | 2005898 A2 | | 12/2008 |
| EP | 2027819 A1 | | 2/2009 |
| EP | 2044890 A1 | | 4/2009 |
| EP | 2055243 A2 | | 5/2009 |
| EP | 2098170 A2 | | 9/2009 |
| EP | 2100561 A2 | | 9/2009 |
| EP | 2100562 A2 | | 9/2009 |
| EP | 2165664 A2 | | 3/2010 |
| EP | 2236098 A2 | | 10/2010 |
| EP | 2263568 A2 | | 12/2010 |
| EP | 2272443 A1 | | 1/2011 |
| EP | 2316345 A1 | | 5/2011 |
| EP | 2324776 A2 | | 5/2011 |
| EP | 2329773 A1 | | 6/2011 |
| EP | 2333509 A1 | | 6/2011 |
| EP | 2462878 A1 | | 6/2012 |
| EP | 2462880 A2 | | 6/2012 |
| EP | 2491872 A1 | | 8/2012 |
| EP | 2586382 A2 | | 5/2013 |
| EP | 2606834 A2 | | 6/2013 |
| EP | 2668910 A2 | | 12/2013 |
| EP | 2676615 A2 | | 12/2013 |
| EP | 2881046 A2 | | 6/2015 |
| ES | 2333509 A1 | | 2/2010 |
| JP | 08-038488 | | 2/1996 |
| JP | 2005-125075 A | | 5/2005 |
| KR | 20120022521 A | | 3/2012 |
| WO | 99/15086 A1 | | 4/1999 |
| WO | 2000/072760 A1 | | 12/2000 |
| WO | 2000/072765 A1 | | 12/2000 |
| WO | 2003/000138 A2 | | 1/2003 |
| WO | 2003/026511 A1 | | 4/2003 |
| WO | 2003/030743 A2 | | 4/2003 |
| WO | 2003065916 A1 | | 8/2003 |
| WO | 2003/077769 A1 | | 9/2003 |
| WO | 2003090630 A1 | | 11/2003 |
| WO | 2004/107989 A1 | | 12/2004 |
| WO | 2006/042210 A2 | | 4/2006 |
| WO | 2007016290 A2 | | 2/2007 |
| WO | 2007/026354 A1 | | 3/2007 |
| WO | 2007137304 A2 | | 11/2007 |
| WO | 2008/131362 A2 | | 10/2008 |
| WO | 2008/133956 A2 | | 11/2008 |
| WO | 2009039506 A1 | | 3/2009 |
| WO | 2007014355 A3 | | 4/2009 |
| WO | 2009/132359 A2 | | 10/2009 |
| WO | 2009/143092 A1 | | 11/2009 |
| WO | 2009149234 A1 | | 12/2009 |
| WO | 2010030114 A2 | | 3/2010 |
| WO | 2011/108840 A2 | | 9/2011 |
| WO | 2012040984 A1 | | 4/2012 |

OTHER PUBLICATIONS

Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
European Office Action corresponding to International Application No. EP 14 15 2236.7 dated Aug. 11, 2015.
Extended European Search Report corresponding to International Application No. EP 15 18 4915.5 dated Jan. 5, 2016.
European Search Report, dated Nov. 13, 2015, corresponding to European Application No. 15173910.9; 6 pages.
Partial European Search Report, dated Apr. 23, 2015, corresponding to European Patent Application No. 14197563.1; 7 pages.

* cited by examiner

ADAPTER ASSEMBLIES FOR INTERCONNECTING ELECTROMECHANICAL HANDLE ASSEMBLIES AND SURGICAL LOADING UNITS

CROSS-REFERENCE TO RELATED APPLICATIONS

This application claims the benefit of and priority to U.S. Provisional Patent Application No. 62/017,539, filed Jun. 26, 2014, the entire disclosure of which is incorporated by reference herein.

BACKGROUND

1. Technical Field

The present disclosure relates to adapter assemblies for electrically and mechanically interconnecting electromechanical handle assemblies and surgical loading units. More specifically, the present disclosure relates to strain sensors of adapter assemblies for sensing an axial force output and/or input of adapter assemblies.

2. Background of Related Art

A number of handle assembly manufacturers have developed product lines with proprietary drive systems for operating and/or manipulating electromechanical surgical instruments. In many instances the electromechanical surgical instruments include a handle assembly, which is reusable, and disposable loading units and/or single use loading units or the like including an end effector disposed at an end thereof that are selectively connected to the handle assembly prior to use and then disconnected from the handle assembly following use in order to be disposed of or in some instances sterilized for re-use.

In certain instances, it is desirable to measure a firing force produced by and/or transmitted through adapter assemblies. This measurement of the firing force can be used, inter alia, to maintain maximum firing force within safe limits and to determine tissue thickness. Accordingly, a need exists for an adapter assembly capable of measuring its axial force output and/or input during operation of an electromechanical surgical instrument.

SUMMARY

The present disclosure relates to adapter assemblies for electrically and mechanically interconnecting electromechanical handle assemblies and surgical loading units, and to force transmitting assemblies disposed within adapter assemblies that are configured to detect and measure an amount of axial force output and/or input of the adapter assembly.

In one embodiment of the present disclosure, a force transmitting assembly of an adapter assembly is provided. The force transmitting assembly includes a rotatable drive shaft, a proximal strain sensor, and a distal drive member. The rotatable drive shaft includes a proximal portion configured to be operatively coupled to a driving member of a handle assembly, a distal portion including a threaded portion, and a flange supported on and extending from the drive shaft. The proximal strain sensor is coupled to the drive shaft and disposed adjacent the flange such that longitudinal movement of the drive shaft imparts a force on the proximal strain sensor via the flange. The distal drive member has a proximal end coupled to the threaded portion of the drive shaft and a distal end configured to be operatively coupled to a driven member of a surgical loading unit. Rotation of the drive shaft longitudinally moves the distal drive member relative to the drive shaft to actuate the surgical loading unit.

In embodiments, the proximal strain sensor may include at least one strain gauge, a plate disposed about the drive shaft, and a mounting member connected to the plate. The mounting member may define a passage therethrough having the drive shaft received therein. The at least one strain gauge may be disposed on the mounting member. The mounting member may be fabricated from a resilient metal material. The at least one strain gauge may include a first set of strain gauges disposed on a proximally-oriented surface of the mounting member and a second set of strain gauges disposed on a distally-oriented surface of the mounting member.

In embodiments, the drive shaft may further include a bearing disposed between the flange and the proximal strain sensor. The proximal portion of the drive shaft may extend through the bearing.

In embodiments, the force transmitting assembly may further include a distal strain sensor, distally spaced from the proximal strain sensor. The flange may be disposed between the proximal and distal strain sensors. The drive shaft may further include a pair of bearings disposed between the proximal and distal strain sensors. The flange may be disposed between the pair of bearings.

In embodiments, the distal portion of the drive shaft may include the flange. The proximal portion of the drive shaft may include another flange. The drive shaft may further include a first bearing disposed between the flange of the distal portion and a distally-oriented surface of the proximal strain sensor and a second bearing disposed between a proximally-oriented surface of the proximal strain sensor and the flange of the proximal portion.

In another embodiment of the present disclosure, an adapter assembly for selectively interconnecting a surgical loading unit and a handle assembly that is configured to actuate the surgical loading unit is provided. The adapter assembly includes a housing, an outer tube, and a force transmitting assembly. The housing is configured and adapted for selective connection with the handle assembly. The outer tube has a proximal end supported by the housing and a distal end configured to be coupled with the surgical loading unit. The force transmitting assembly extends at least partially through the outer tube. The force transmitting assembly includes a rotatable drive shaft, a proximal strain sensor, and a distal drive member. The rotatable drive shaft includes a proximal portion configured to be operatively coupled to a rotatable driving member of the handle assembly, a distal portion including a threaded portion, and a flange supported on and extending from the drive shaft. The proximal strain sensor is coupled to the drive shaft and affixed to the housing. The proximal strain sensor is disposed adjacent the flange such that longitudinal movement of the drive shaft imparts a force on the proximal strain sensor via the flange. The distal drive member has a proximal end coupled to the threaded portion of the drive shaft and a distal end configured to be operatively coupled to a translatable driven member of the surgical loading unit. Rotation of the drive shaft longitudinally moves the distal drive member relative to the drive shaft to actuate the surgical loading unit.

In embodiments, the proximal strain sensor may further include a plate disposed about the drive shaft and affixed to the housing.

In yet another embodiment of the present disclosure, a surgical instrument is provided. The surgical instrument includes a handle assembly, an adapter assembly, and a surgical loading unit. The handle assembly includes a rotatable driving member. The adapter assembly includes a housing coupled with the handle assembly, an outer tube having a proximal end supported by the housing and a distal end, and a force transmitting assembly extending at least partially through the outer tube. The force transmitting assembly includes a rotatable drive shaft, a proximal strain sensor, and a distal drive member. The rotatable drive shaft includes a proximal portion operatively coupled to the rotatable driving member of the handle assembly and a distal portion including a flange and a threaded portion. The proximal strain sensor is coupled to the drive shaft and affixed to the housing. The proximal strain sensor is disposed adjacent the flange such that longitudinal movement of the drive shaft imparts a force on the proximal strain sensor via the flange. The distal drive member has a proximal end coupled to the threaded portion of the drive shaft and a distal end. The surgical loading unit is configured to be actuated by the handle assembly. The surgical loading unit includes a translatable driven member operatively coupled to the distal end of the distal drive member of the force transmitting assembly. Rotation of the drive shaft longitudinally moves the distal drive member relative to the driv

BRIEF DESCRIPTION OF THE DRAWINGS

Embodiments of the present disclosure are described herein with reference to the accompanying drawings, wherein.

DETAILED DESCRIPTION

Figure 1A:
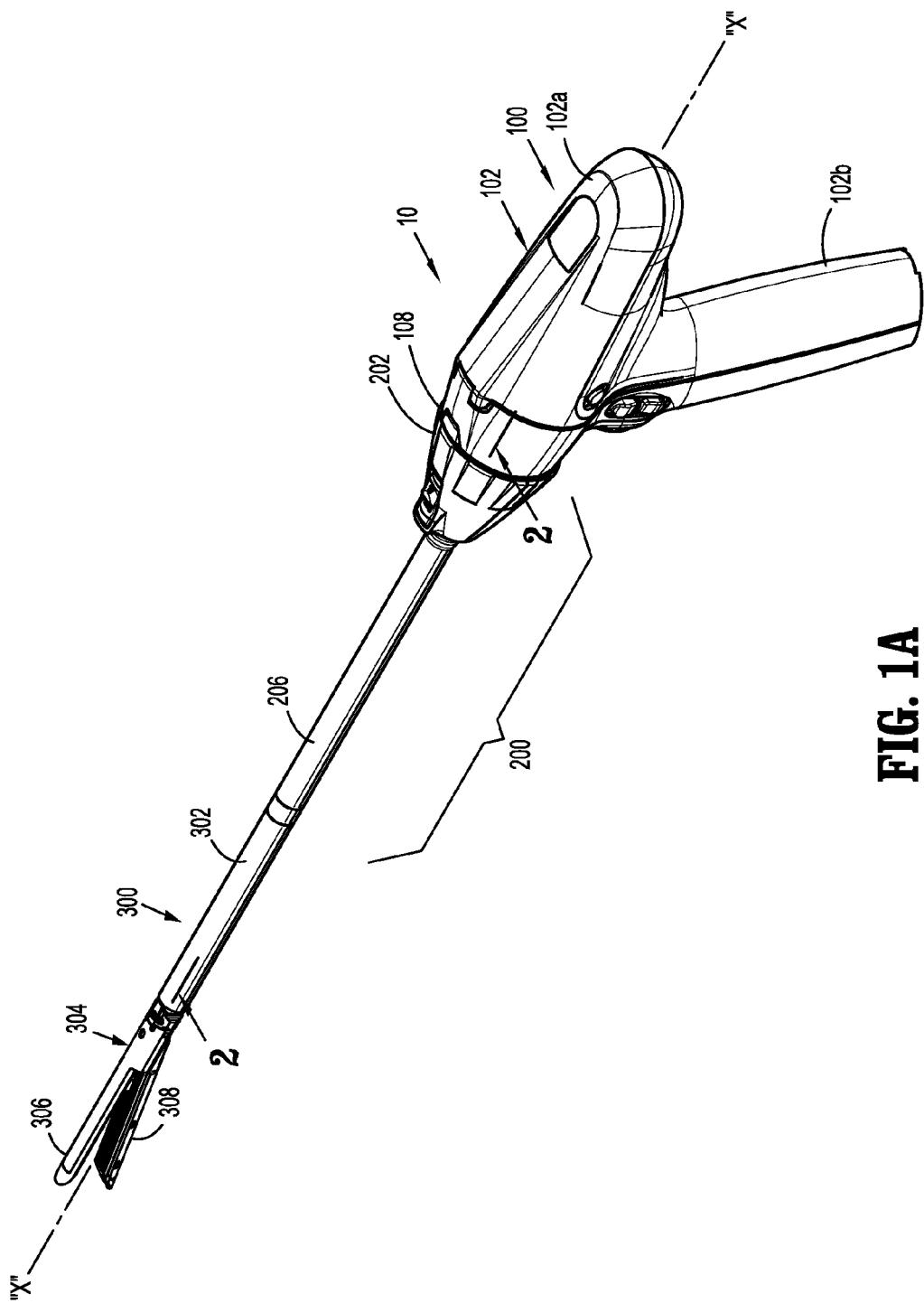
FIG. 1A is a perspective view of a surgical instrument including an adapter assembly, in accordance with an embodiment of the present disclosure, interconnected between an exemplary electromechanical handle assembly and a surgical loading unit.

Embodiments of the presently disclosed electromechanical surgical instruments including handle assemblies, adapter assemblies, and surgical loading units are described in detail with reference to the drawings, in which like reference numerals designate identical or corresponding elements in each of the several views. As used herein the term "distal" refers to that portion of the handle assembly, adapter assembly, surgical loading unit, or component thereof, farther from the user, while the term "proximal" refers to that portion of the handle assembly, adapter assembly, surgical loading unit, or component thereof, closer to the user.

A surgical instrument, in accordance with an embodiment of the present disclosure, is generally designated as 10, and is in the form of a powered hand held electromechanical surgical instrument configured for clamping and/or sealing tissue. Surgical instrument 10 includes a handle assembly 100, an adapter assembly 200, and a surgical loading unit 300. Handle assembly 100 is configured for selective coupling, via adapter assembly 200, to a plurality of different surgical loading units, such as, for example, surgical loading unit 300. Each surgical loading unit is configured for actuation and manipulation by powered handle assembly 100. Adapter assembly 200 includes a force transmitting assembly 220 (see FIGS. 2, 3, 4A, and 4B) disposed therein having at least one strain sensor 240 including at least one strain gauge configured to detect and measure an axial force output and/or input of adapter assembly 200 during operation thereof, as described herein.

Figure 1B:
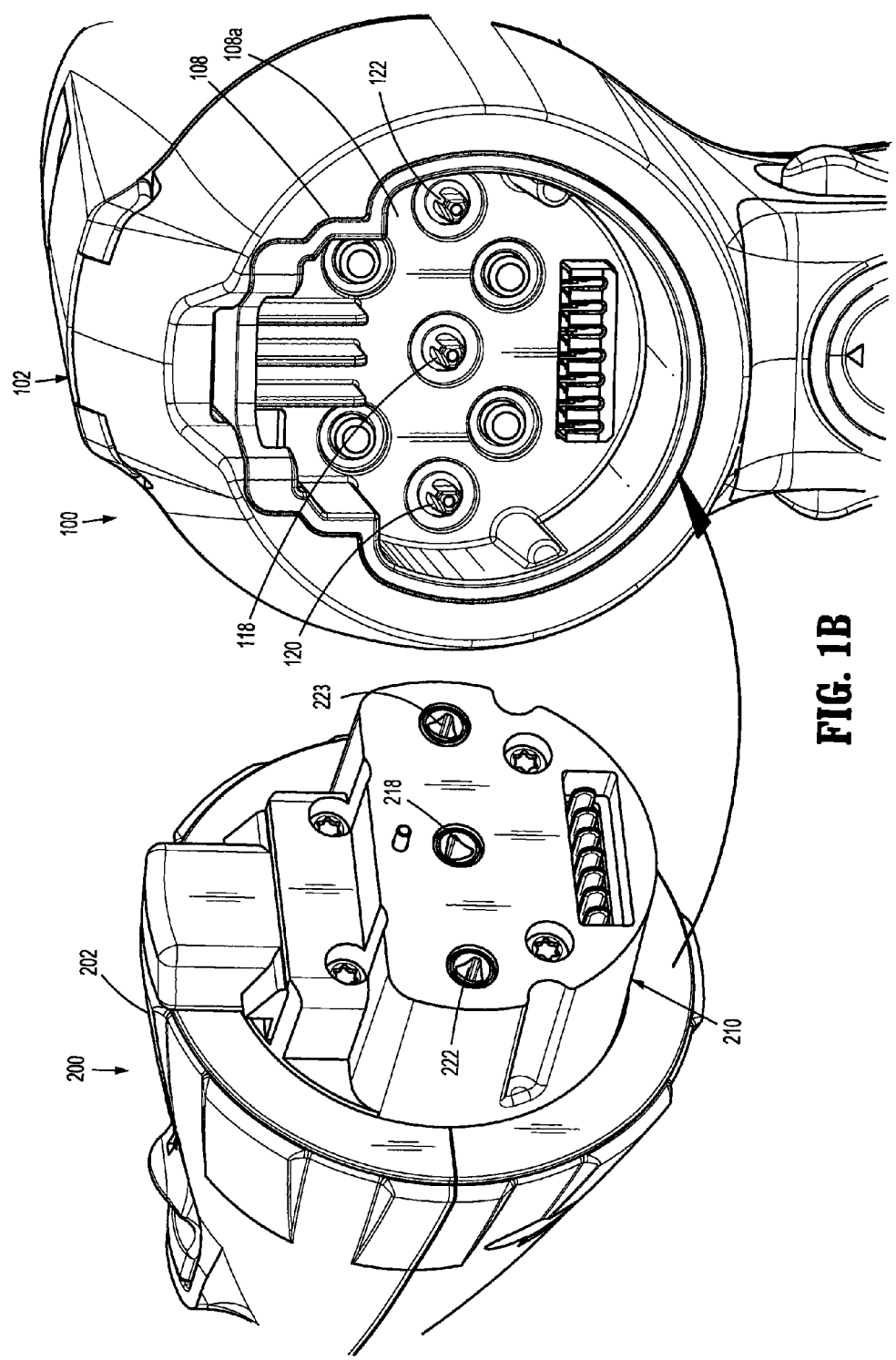
FIG. 1B is a perspective view illustrating an attachment of a proximal end of the adapter assembly to a distal end of the electromechanical handle assembly of FIG. 1A.

As illustrated in FIGS. 1A and 1B, handle assembly 100 includes a handle housing 102 including a circuit board (not shown), and a drive mechanism (not shown) is situated therein. The circuit board is configured to control the various operations of surgical instrument 10. Handle housing 102 defines a cavity therein (not shown) for selective removable receipt of a rechargeable battery (not shown) therein. The battery is configured to supply power to any of the electrical components of surgical instrument 10.

Handle housing 102 includes an upper housing portion 102a which houses various components of handle assembly 100, and a lower hand grip portion 102b extending from upper housing portion 102a. Lower hand grip portion 102b may be disposed distally of a proximal-most end of upper housing portion 102a. Handle housing 102 provides a housing in which the drive mechanism is situated. The drive mechanism is configured to drive shafts and/or gear components in order to perform the various operations of surgical instrument 10. In particular, the drive mechanism is configured to drive shafts and/or gear components in order to selectively move a tool assembly 304 of loading unit 300 relative to a proximal body portion 302 of loading unit 300, to rotate loading unit 300 about a longitudinal axis "X" relative to handle assembly 100, to move/approximate an anvil assembly 306 and/or a cartridge assembly 308 of loading unit 300 relative to one another, and/or to fire a stapling and cutting cartridge within cartridge assembly 308 of loading unit 300.

As illustrated in FIG. 1B, handle housing 102 defines a connecting portion 108 configured to accept a corresponding drive coupling assembly 210 of adapter assembly 200. Specifically, connecting portion 108 of handle assembly 100 has a recess 108a that receives a component of drive coupling assembly 210 of adapter assembly 200 when adapter assembly 200 is mated to handle assembly 100. Connecting portion 108 houses three rotatable, motorized drive connectors 118, 120, 122, which are arranged in a common plane or line with one another.

When adapter assembly 200 is mated to handle assembly 100, each of rotatable drive connectors 118, 120, 122 of handle assembly 100 couples with a corresponding rotatable connector sleeve 218, 223, 222 of adapter assembly 200. In this regard, the interface between corresponding first drive connector or driving member 118 and first connector sleeve 218, the interface between corresponding second drive connector 120 and second connector sleeve 223, and the interface between corresponding third drive connector 122 and third connector sleeve 222 are keyed such that rotation of each of drive connectors 118, 120, 122 of handle assembly 100 causes a corresponding rotation of the corresponding connector sleeve 218, 223, 222 of adapter assembly 200.

The mating of drive connectors 118, 120, 122 of handle assembly 100 with connector sleeves 218, 223, 222 of adapter assembly 200 allows rotational forces to be independently transmitted via each of the three respective connector interfaces. The drive connectors 118, 120, 122 of handle assembly 100 are configured to be independently rotated by the drive mechanism of handle assembly 100. In this regard, a function selection module (not shown) of the drive mechanism selects which drive connector or connectors 118, 120, 122 of handle assembly 100 is to be driven by a motor (not shown) of handle assembly 100.

Since each of drive connectors 118, 120, 122 of handle assembly 100 has a keyed and/or substantially non-rotatable interface with respective connector sleeves 218, 223, 222 of adapter assembly 200, when adapter assembly 200 is coupled to handle assembly 100, rotational force(s) are selectively transferred from drive connectors of handle assembly 100 to adapter assembly 200.

The selective rotation of drive connector(s) 118, 120 and/or 122 of handle assembly 100 allows handle assembly 100 to selectively actuate different functions of loading unit 300. For example, selective and independent rotation of first drive connector or rotatable driving member 118 of handle assembly 100 corresponds to the selective and independent opening and closing of tool assembly 304 of loading unit 300, and driving of a stapling/cutting component of tool assembly 304 of loading unit 300. As an additional example, the selective and independent rotation of second drive connector 120 of handle assembly 100 corresponds to the selective and independent articulation of tool assembly 304 of loading unit 300 transverse to longitudinal axis "X" (see FIG. 1A). Additionally, for instance, the selective and independent rotation of third drive connector 122 of handle assembly 100 corresponds to the selective and independent rotation of loading unit 300 about longitudinal axis "X" (see FIG. 1A) relative to handle housing 102 of handle assembly 100.

Reference may be made to International Pub. No. WO 2009/039506 and U.S. Patent Publication No. 2011/0121049, the entire contents of each of which being incorporated herein by reference, for a detailed description of various internal components of and operation of exemplary electromechanical handle assembly 100.

With continued reference to FIG. 1B, adapter assembly 200 is configured for selectively interconnecting a surgical loading unit, for example, surgical loading unit 300 and a handle assembly, for example, handle assembly 100. Adapter assembly 200 is configured to convert a rotation of either of drive connectors 118, 120 and 122 of handle assembly 100 into axial translation useful for operating loading unit 300.

Figure 2:
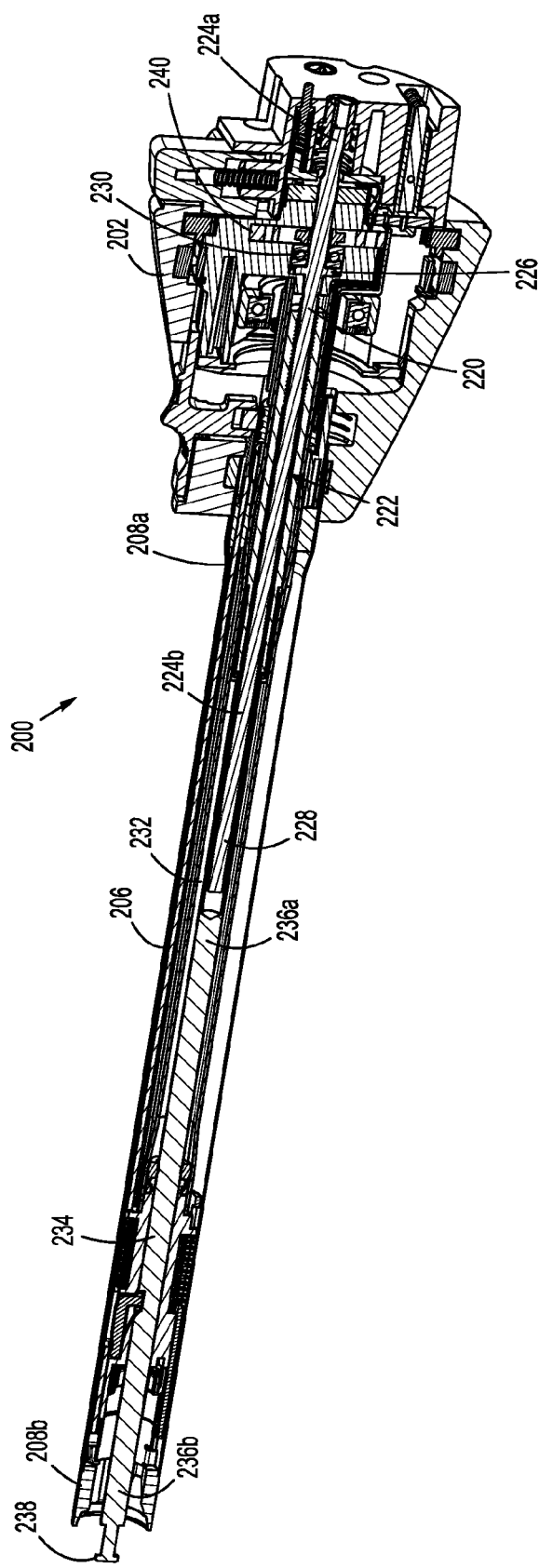
FIG. 2 is a cross-sectional view of the adapter assembly as taken along section line 2-2 of FIG. 1A.

With reference to FIG. 2, adapter assembly 200 generally includes a housing, such as, for example, a knob housing 202 and an outer tube 206 extending from a distal end of knob housing 202. Knob housing 202 and outer tube 206 are configured and dimensioned to house the components of adapter assembly 200. Outer tube 206 is dimensioned for endoscopic insertion, in particular, outer tube 206 is passable through a typical trocar port, cannula or the like. Knob housing 202 is dimensioned to not enter the trocar port, cannula of the like. Knob housing 202 is configured and adapted to connect to connecting portion 108 (FIG. 1B) of handle housing 102 of handle assembly 100. Outer tube 206 has a proximal end 208a supported by knob housing 202 and a distal end 208b configured to be selectively attached to surgical loading unit 300.

With continued reference to FIG. 2, adapter assembly 200 includes a force/rotation transmitting/converting assembly 220 supported within knob housing 202 and extending through outer tube 206. Force transmitting assembly 220 is configured and adapted to transmit/convert a speed/force of rotation (e.g., increase or decrease) of rotatable driving member 118 of handle assembly 100 into an axial force before such rotational speed/force is transmitted to surgical loading unit 300. Specifically, force transmitting assembly 220 is configured and adapted to transmit or convert a rotation of driving member 118 of handle assembly 100 into axial translation of a translatable driven member 312 (FIG. 5) of surgical loading unit 300 to effectuate articulation, closing, opening and/or firing of loading unit 300.

Figure 5:
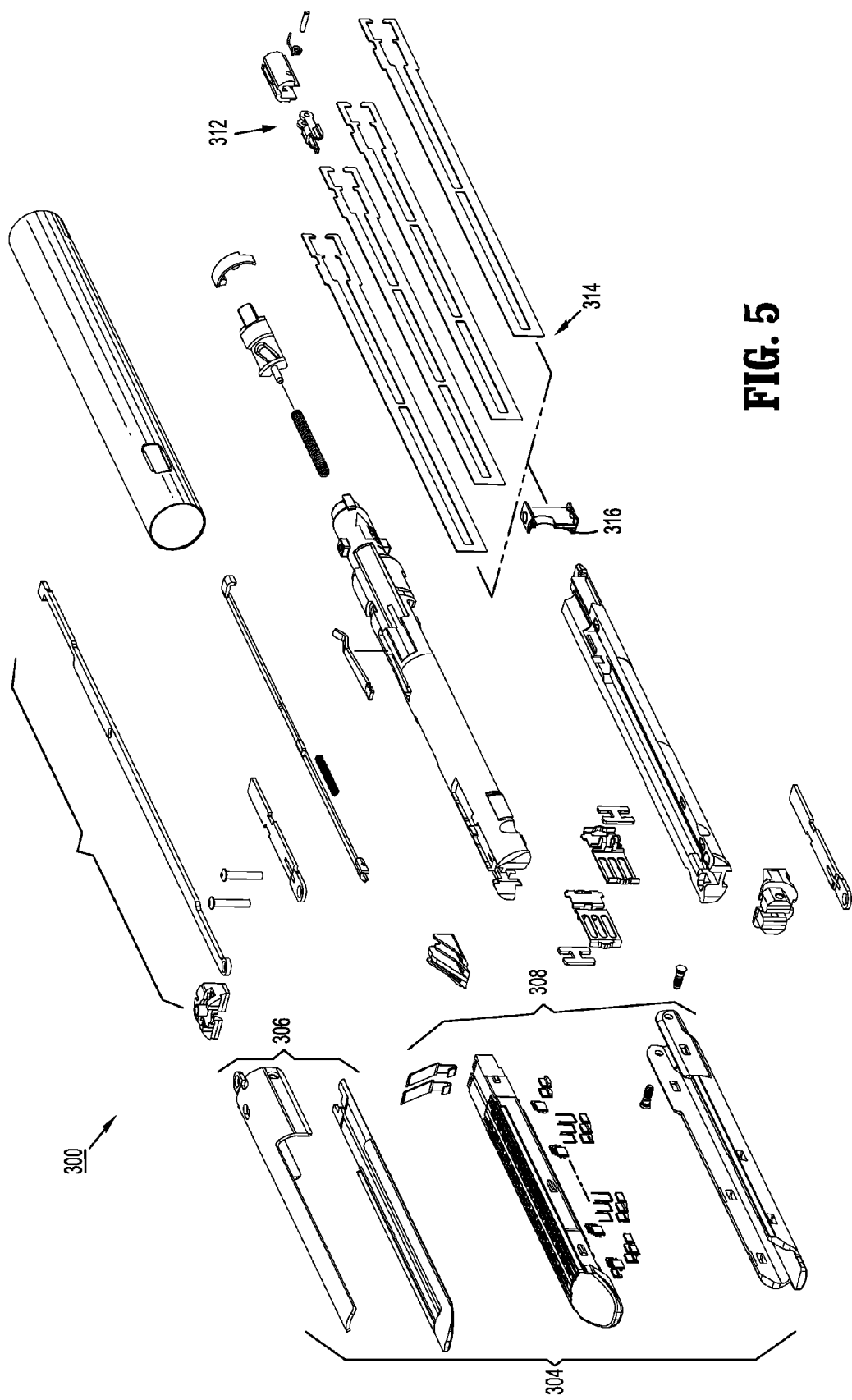
FIG. 5 is an exploded view of a surgical loading unit in accordance with the principles of the present disclosure.

Reference may be made to U.S. Patent Publication No. 2009/0314821, filed on Aug. 31, 2009, entitled "TOOL ASSEMBLY FOR A SURGICAL STAPLING DEVICE" for a detailed discussion of the construction and operation of loading unit 300, as illustrated in FIG. 5.

Figure 3:
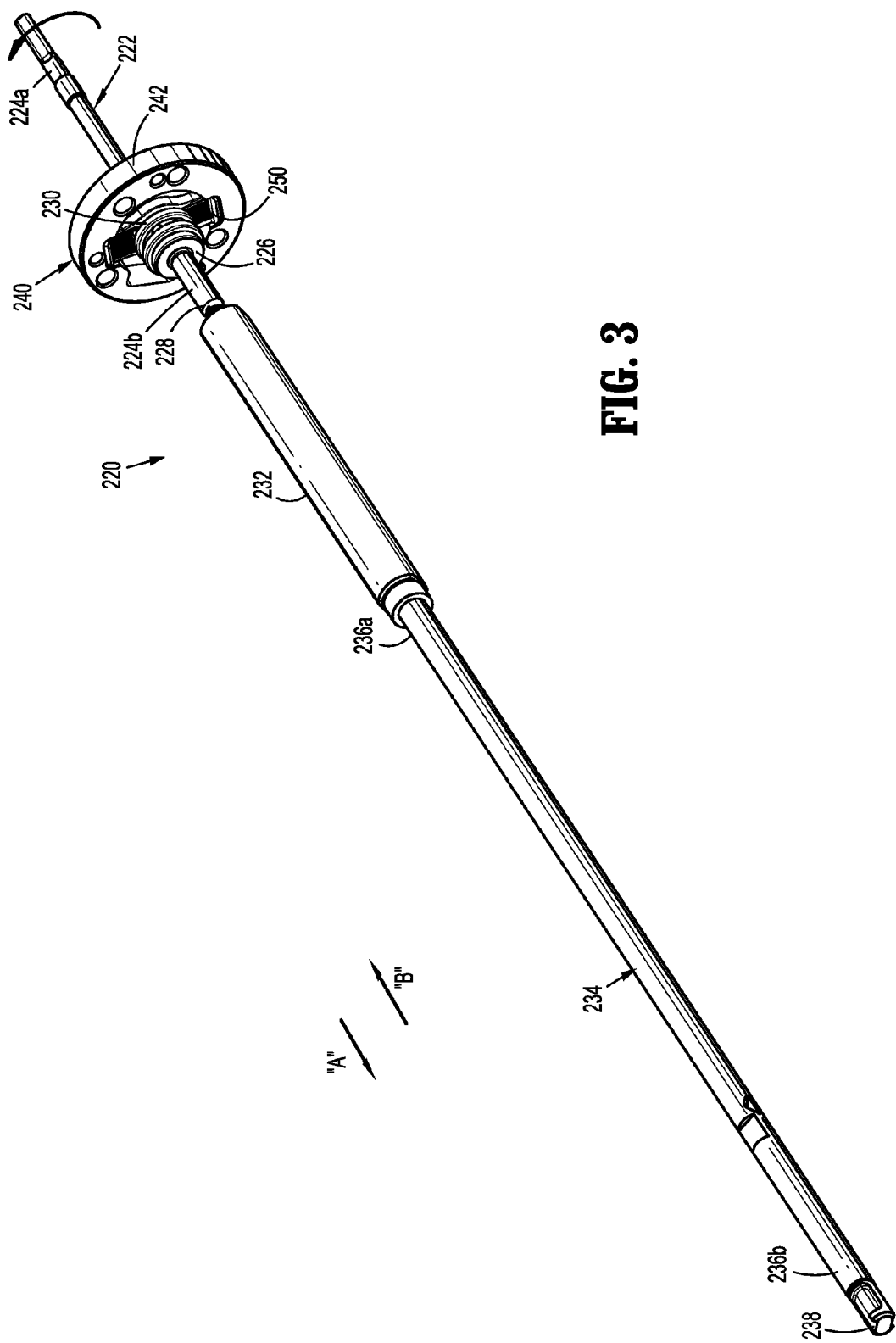
FIG. 3 is perspective view of a force transmitting assembly of the adapter assembly of FIG. 2.

As shown in FIGS. 2 and 3, force transmitting assembly 220 includes a rotatable drive shaft 222 disposed within knob housing 202, a strain sensor 240 coupled to drive shaft 222, and a distal drive member 234 coupled to a distal portion 224b of drive shaft 222. Drive shaft 222 includes a proximal portion 224a configured to be operatively coupled to driving member 118 of handle assembly 100 via first connector 218. Drive shaft 222 includes distal portion 224b having a flange 226 affixed thereto and a threaded portion 228. Proximal and distal portions 224a, 224b of drive shaft 222 are non-rotatable connected to one another.

Drive shaft 222 further includes a bearing 230 in abutment with a proximally-oriented side of flange 226. Drive shaft 222 extends through bearing 230. Bearing 230 is configured to reduce friction (i.e., enhance relative rotation) between flange 226 of drive shaft 222 and strain sensor 240 by axially spacing flange 226 from strain sensor. In some embodiments, bearing 230 may be in the form of various bearings, such as, for example, a thrust bearing.

Force transmitting assembly 220 includes a drive coupling nut 232 rotatably coupled to threaded portion 228 of drive shaft 222, and which is slidably disposed within outer tube 206 of adapter assembly 200. Drive coupling nut 232 is slidably keyed within outer tube 206 so as to be prevented from rotation as drive shaft 222 is rotated. In this manner, as drive shaft 222 is rotated, drive coupling nut 232 is translated along threaded portion 228 of drive shaft 222 and, in turn, through and/or along outer tube 206.

Distal drive member 234 has a proximal end 236a coupled to distal portion 224b of drive shaft 222 via mechanical engagement with drive coupling nut 232, such that axial movement of drive coupling nut 232 results in a corresponding amount of axial movement of distal drive member 234. Distal drive member 234 has a distal end 236b configured to be operatively coupled to translatable driven member 312 (FIG. 5) of surgical loading unit 300. In particular, distal end 236b of distal drive member 234 supports a connection member 238 configured and dimensioned for selective engagement with translatable driven member 312 (FIG. 5) of loading unit 300. Drive coupling nut 232 and/or distal drive member 234 function as a force transmitting member to components of loading unit 300.

In use, as drive shaft 222 is rotated, due to a rotation of first connector sleeve 218, as a result of the rotation of rotatable driving member 118 of handle assembly 100, drive coupling nut 232 is caused to be translated within outer tube 206. As drive coupling nut 232 is caused to be translated axially, distal drive member 234 is caused to be translated axially within outer tube 206. As distal drive member 234 is translated axially in a distal direction, with connection member 238 connected thereto and engaged with translatable driven member 312 of a drive assembly 314 of loading unit 300 (FIG. 5), distal drive member 234 causes concomitant axial translation of translatable driven member 312 of loading unit 300 to effectuate a closure of tool assembly 304 and a firing of tool assembly 304 of loading unit 300.

With specific reference to FIGS. 3, 4A, and 4B, strain sensor 240 is designed and adapted to detect, measure, and relay to handle assembly 100 an axial force output and/or input of adapter assembly 200, as described in greater detail below. Strain sensor 240 is coupled to drive shaft 222 and disposed adjacent flange 226 such that proximal, longitudinal movement of distal portion 224b of drive shaft 222 imparts a force on strain sensor 240 via flange 226. Strain sensor 240 includes a plate 242 disposed about drive shaft 222 and affixed to knob housing 202 (see FIG. 2) such that strain sensor 240 is prevented from moving axially within knob housing 202. It is contemplated that plate 242 is axially constrained within knob housing 202 via welding, fasteners, frictional engagement, snap-fit engagement, or the like. Plate 242 includes a central opening 244 extending therethrough configured to receive a mounting member 250 therein as described in more detail below. Plate 242 further includes a plurality of holes 246 extending through a thickness thereof for mounting and clearance purposes.

Strain sensor 240 further includes a mounting member or plate 250 connected to plate 242. Mounting member 250 may be variously configured, such as, for example, as an I-beam or a cylinder. Mounting member 250 has a first end 252a fixed to a first inner radial edge of plate 242 and a second end 252b fixed to a second inner radial edge of plate 242 such that mounting member 250 extends across central opening 244 of plate 242. Mounting member 250 further includes a central portion 254 defining a passage 256 therethrough having drive shaft 222 movably received therein. Central portion 254 of mounting member 250 is in abutment with a proximally-oriented side of bearing 230 such that proximal, longitudinal movement of bearing 230 along longitudinal axis "X" imparts an axial force on central portion 254. Mounting member 250 is configured to flex relative to first and second ends 252a, 252b thereof upon an axial force being imparted on central portion 254. Mounting member 250 may be fabricated from a resilient metal material, shape-memory material, or the like, to allow for flexion thereof.

Figure 4A:
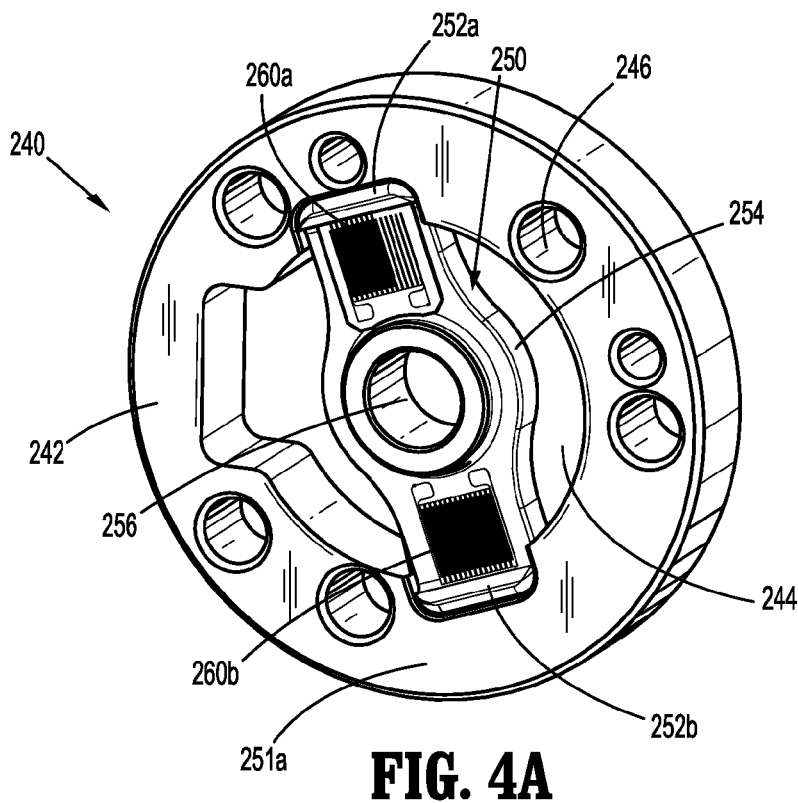
FIGS. 4A and 4B are front and rear perspective views, respectively, of a strain sensor of the force transmitting assembly shown in FIG. 3.
Figure 4B:
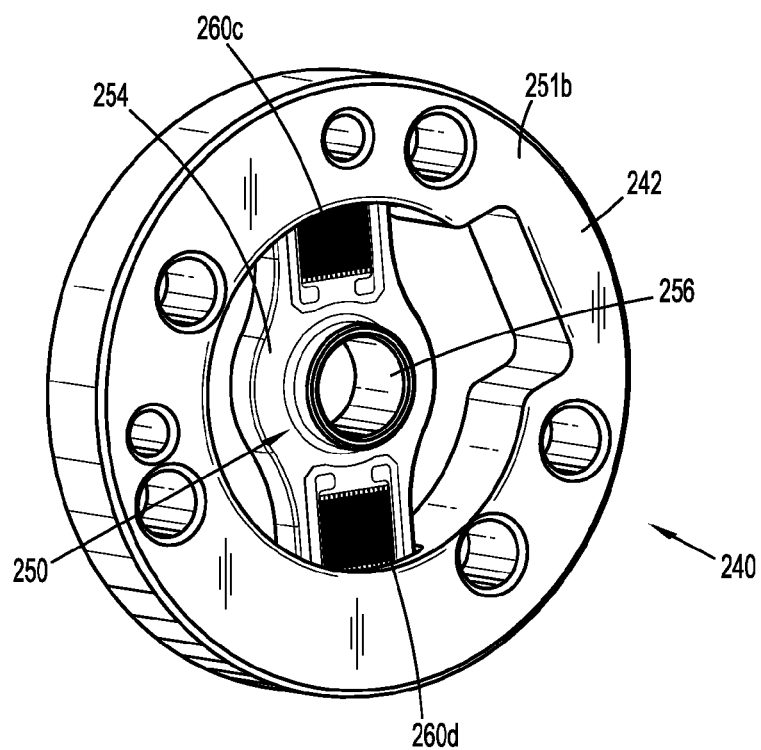

With reference to FIGS. 4A and 4B, strain sensor 240 further includes at least one or a plurality of strain gauges 260a, 260b, 260c, 260d electrically connected to a circuit board (not shown) and disposed or mounted on mounting member 250. Strain gauges 260a, 260b, 260c, 260d detect and measure an axial force output of adapter assembly 200, as described in greater detail below. A first set of strain gauges 260a, 260b (FIG. 4A) is disposed on a distally-oriented surface 251a of mounting member 250 and a second set of strain gauges 260c, 260d (FIG. 4B) is disposed on a proximally-oriented surface 251b of mounting member 250. In this way, as mounting member 250 is flexed/bent/bowed proximally due to a proximally-oriented axial force imparted thereon, first set of strain gauges 260a, 260b are compressed and second set of strain gauges 260c, 260d are tensioned. Similarly, if mounting member 250 is flexed/bent/bowed distally due to a distally-oriented axial force imparted thereon, first set of strain gauges 260a, 260b are tensioned and second set of strain gauges 260c, 260d are compressed. In embodiments, mounting member 250 may include a cutout (not shown) for measurement of tension and compression on distally-oriented surface 251b of mounting member 250.

As strain gauges 260a, 260b, 260c, 260d are compressed and/or tensioned conditions, an electrical resistance of each strain gauge 260a, 260b, 260c, 260d is changed, which is measured by a circuit board, such as, for example, a wheatstone bridge (not shown). The measured change in electrical resistance of each strain gauge 260a, 260b, 260c, 260d is then related to the amount strain gauges 260a, 260b, 260c, 260d have been strained using calculations within the purview of those skilled in the art. The calculated strain is then correlated to an amount of axial force output of adapter assembly 200.

In some embodiments, each of strain gauges 260a, 260b, 260c, 260d is fabricated using a thin-film sputtering deposition process. In particular, a dielectric layer is applied to mounting member 250 to insulate circuit power from the underlying metal mounting member 250. A thin film of resistive alloy is sputtered over the dielectric layer to form each strain gauge 260a, 260b, 260c, 260d. In further embodiments, strain gauges 260a, 260b, 260c, 260d may be in the form of semiconductor strain gauges (e.g., piezoresistors), foil gauges, or the like. In embodiments, strain gauges 260a, 260b, 260c, 260d are incorporated into mounting member 250.

In operation, strain gauges 260a, 260b, 260c, 260d detect and measure an axial force output of adapter assembly 200 during operation of handle assembly 100. Handle assembly 100 is actuated to carry out various functions of surgical loading unit 300. As handle assembly 100 is actuated, drive shaft 222 of force transmitting assembly 220 is rotated relative to coupling nut 232 to axially move coupling nut 232 in a distal direction relative to drive shaft 222. Distal movement of coupling nut 232 longitudinally moves distal drive member 234 of force transmitting assembly 220 relative to drive shaft 222 resulting in a force, applied in a direction indicated by arrow "A" in FIG. 3, to translatable driven member 312 (FIG. 5) of surgical loading unit 300. An equal and opposite reactive force is exerted by translatable driven member 312 of surgical loading unit 300, in a direction indicated by arrow "B" in FIG. 3, on distal drive member 234. The reactive force exerted on distal drive member 234 is transmitted in a proximal direction along force transmitting assembly 220 to flange 226 of drive shaft 222 and, in turn, flange 226 of drive shaft 222 transmits the reactive force to central portion 254 of mounting member 250 of strain sensor 240 via bearing 230.

Due to the resilient properties of mounting member 250, and plate 242 of strain sensor 240 being axially fixed with knob housing 202, central portion 254 flexes/bends/bows proximally relative to plate 242 such that first set of strain gauges 260a, 260b stretch, and second set of strain gauges 260c, 260d compress. Strain gauges 260a, 260b, 260c, 260d detect and measure the amount of strain they undergo, such that an amount of stress imparted on strain sensor 240 can be calculated. The axial force output of adapter assembly 200 is then calculated using the calculated amount of stress imparted on strain sensor 240.

Knowing the amount of axial force output of adapter assembly 200 can be used to, inter alia, prevent further actuation of loading unit 300 upon reaching a threshold amount of axial output force deemed unsafe, determine the amount of force needed to retract the knife bar (not shown)

after actuating loading unit 300, and/or measure the amount of force needed to clamp tissue so as to determine tissue thickness, which can allow a clinician to determine whether tissue is too thick or thin for a particular surgical loading unit. The information made available by strain sensor 240 can also be used to indicate to a clinician that knife bar (not shown) has reached an end or a stop of loading unit 300 or a firing sled (not shown) of loading unit 300 has reached an end or stop of staple cartridge 308. Reference may be made to U.S. Pat. No. 8,517,241, the entire contents of which is incorporated herein by reference, for a more detailed description of uses of information provided by strain sensor 240.

Figure 6:
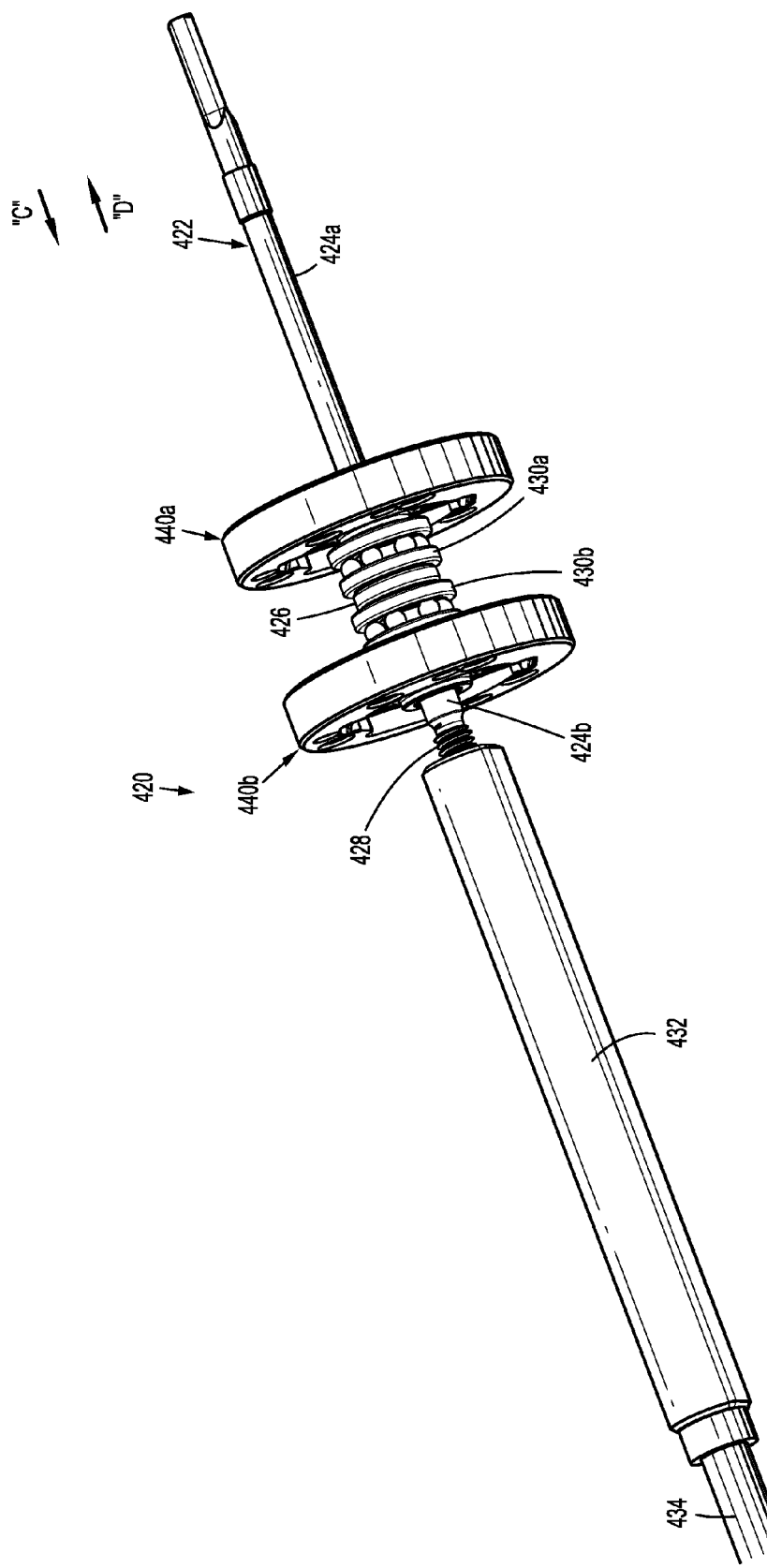
FIG. 6 is a partial perspective view of another embodiment of a force transmitting assembly disposable within the adapter assembly of FIG. 2.

In another embodiment, as illustrated in FIG. 6, a force transmitting assembly 420 is provided, similar to force transmitting assembly 220 described above. Force transmitting assembly 420 is a component of an adapter assembly, such as, for example, adapter assembly 200 shown in FIG. 2. Force transmitting assembly 420 includes a rotatable drive shaft 422, a pair of strain sensors 440a, 440b coupled to drive shaft 422, and a distal drive member 434 coupled to a distal portion 424b of drive shaft 422.

Drive shaft 422 includes a proximal portion 424a configured to be operatively coupled to driving member 118 of handle assembly 100 via first connector 218. Proximal portion 424a further includes a proximal strain sensor 440a, similar to strain sensor 240 described above, disposed at a distal end thereof. Drive shaft 422 includes a distal portion 424b having a distal strain sensor 440b, similar to strain sensor 240 described above, distally spaced from proximal strain sensor 440a. Distal portion 424b includes a threaded portion 428 disposed at a distal end thereof configured for threaded coupling with a proximal end of a coupling nut 432. Drive shaft 422 further includes a flange 426 disposed between proximal and distal strain sensors 440a, 440b. Flange 426 interconnects proximal and distal portions 424a, 424b of drive shaft 422.

Drive shaft 422 further includes a pair of bearings 430a, 430b disposed between proximal and distal strain sensors 440a, 440b. First bearing 430a is captured between a distally-oriented side of proximal strain sensor 440a and a proximally-oriented side of flange 426. Second bearing 430b is captured between a distally-oriented side of flange 426 and a proximally-oriented side of distal strain sensor 440b. Flange 426 of drive shaft 422 is disposed between bearings 430a, 430b, spaced from proximal and distal strain sensors 440a, 440b by bearings 430a, 430b. In this way, bearings 430a, 430b act to reduce friction (i.e., enhance relative rotation) between flange 426 of drive shaft 422 and proximal strain sensor 440a and between flange 426 of drive shaft 422 and distal strain sensor 440b.

In operation, strain sensor 440 is able to detect and measure both firing and retraction forces of adapter assembly 200, in which strain sensor 440 is situated. Strain gauges (not shown), similar to strain gauges 260a, 260b, 260c, 260d, of proximal and distal strain sensors 440a, 440b, detect and measure an axial force output of adapter assembly 200 during operation of handle assembly 100. Handle assembly 100 is actuated to carry out various functions of surgical loading unit 300. As handle assembly 100 is actuated, drive shaft 422 of force transmitting assembly 420 is rotated relative to coupling nut 432 to axially move coupling nut 432 in a distal direction relative to drive shaft 422. Distal movement of coupling nut 432 longitudinally moves distal drive member 434 of force transmitting assembly 420 relative to drive shaft 422 resulting in a force, applied in a direction indicated by arrow "C" in FIG. 6, to translatable driven member 312 of surgical loading unit 300 (FIG. 5). An equal and opposite reactive force is exerted, in a direction indicated by arrow "D" in FIG. 6, on distal drive member 434 by translatable driven member 312 of surgical loading unit 300.

The reactive force exerted on distal drive member 434 is transmitted in a proximal direction along force transmitting assembly 420 to flange 426 of drive shaft 422 and, in turn, flange 426 of drive shaft 422 transmits the force to proximal strain sensor 440a through first bearing 430a. This force causes the strain gauge (not shown) of proximal strain sensor 440a to strain. The strain gauge detects and measures the amount of this strain, such that an amount of stress imparted on proximal strain sensor 440a can be calculated. The axial force output of adapter assembly 200 is then calculated using the calculated amount of stress imparted on proximal strain sensor 440a.

As mentioned above, force transmitting assembly 420 is also configured to detect and measure an amount of force required to retract a knife 316 (FIG. 5) of surgical loading unit 300. In operation, a force, applied in a direction indicated by arrow "D" in FIG. 6 to drive shaft 422, is transmitted distally along force transmitting assembly 420 to flange 426 of drive shaft 422 and, in turn, flange 426 of drive shaft 422 transmits the force to distal strain sensor 440b through second bearing 440b. This force causes a strain gauge (not shown), similar to strain gauges 260a, 260b, 260c, 260d, of distal strain sensor 440b to strain. The strain gauge detects and measures the amount of strain it undergoes, such that an amount of stress imparted on distal strain sensor 440b can be calculated. The retraction force of adapter assembly 200 is then calculated using the calculated amount of stress imparted on distal strain sensor 440b.

Figure 7:
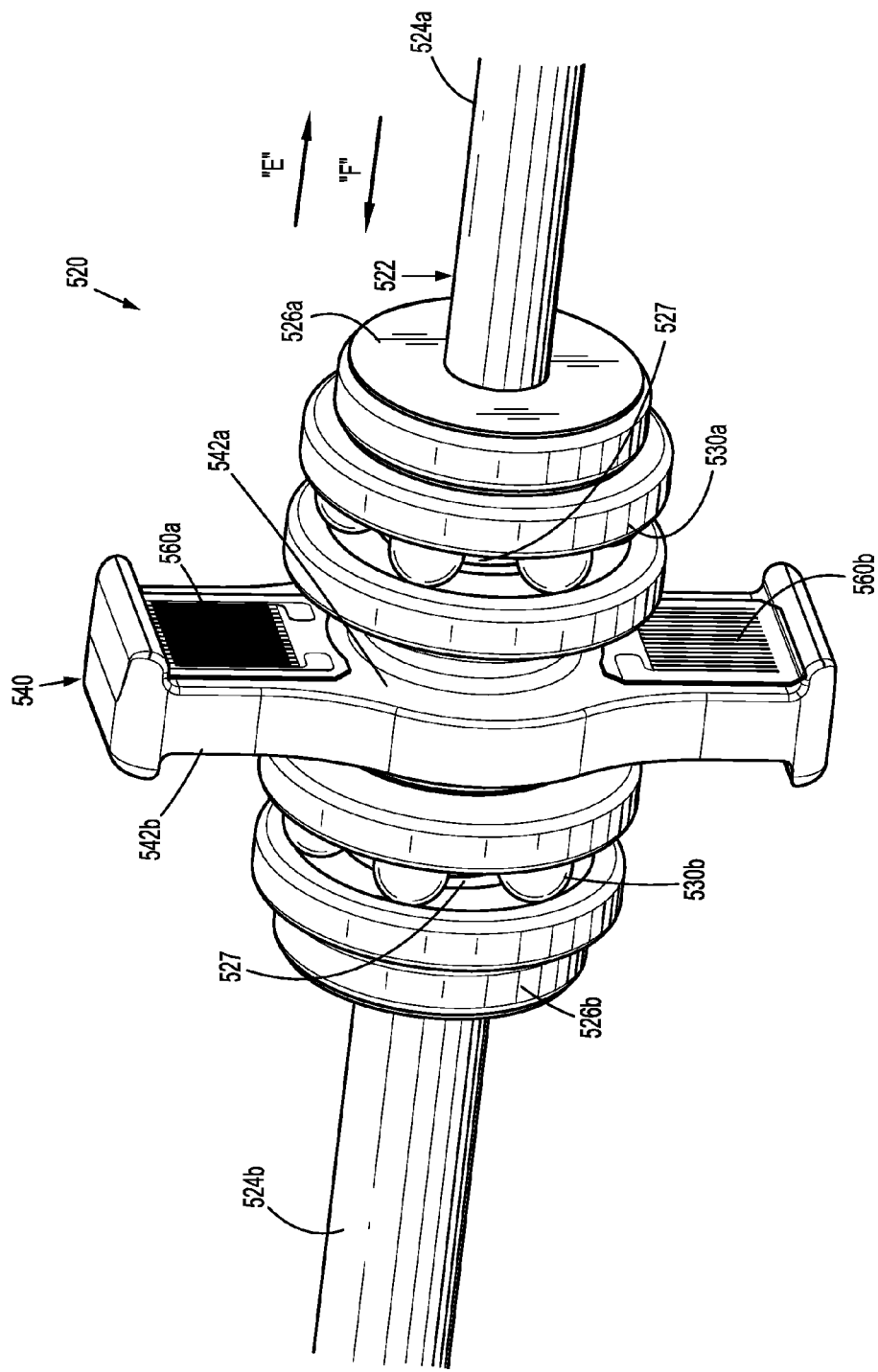
FIG. 7 is an enlarged, partial view of yet another embodiment of a force transmitting assembly disposable within the adapter assembly of FIG. 2.

In yet another embodiment, as illustrated in FIG. 7, a force transmitting assembly 540 is provided, similar to force transmitting assembly 440 described with regard to FIG. 6. Force transmitting assembly 540 includes a rotatable drive shaft 522. Drive shaft 522 includes a proximal portion 524a configured to be operatively coupled to driving member 118 of handle assembly 100 via first connector 218. Proximal portion 524a of drive shaft 522 further includes a flange 526a disposed at a distal end thereof. Drive shaft 522 includes a distal portion 524b having a flange 526b disposed at a proximal end thereof.

Drive shaft 522 further includes a pair of bearings 530a, 530b and a strain sensor 540, similar to strain sensor 240 described above, each disposed between flanges 526a, 526b of proximal and distal portions 524a, 524b of drive shaft 522. Strain sensor 540 includes a pair of strain gauges 560a, 560b, similar to strain gauges 260a, 260b described above. First bearing 530a is captured between a distally-oriented side of flange 526a of proximal portion 524a of drive shaft 522 and a proximally-oriented side 542a of strain sensor 540. Second bearing 530b is captured between a distally-oriented side 542b of strain sensor 540 and a proximally-oriented side of flange 526b of distal portion 524b of drive shaft 522. Bearings 530a, 530b act to reduce friction (i.e., enhance relative rotation) between proximally-oriented side 542a of strain sensor 540 and flange 526a of drive shaft 522 and between distally-oriented side 542b of strain sensor 540 and flange 526b of drive shaft 522, respectively. Drive shaft 522 includes a bar or shaft 527 that extends through bearings 530a, 530b and strain sensor 540 to interconnect flange 526a of proximal portion 524a of drive shaft 522 to flange 526b of distal portion 524b of drive shaft 522, such that proximal and distal portions 524a, 524b of drive shaft 522 are non-rotatably connected.

In operation, strain sensor 540 is able to detect and measure both firing and retraction forces of adapter assembly 200, in which strain sensor 540 is situated. Specifically, a force is applied, in a direction indicated by arrow "E" in FIG. 7, to distal portion 524*b* of drive shaft 522. Flange 526*b* of distal portion 524*b* of drive shaft 522 transmits the force to strain sensor 540 through second bearing 530*b*. This force causes strain gauges 560*a*, 560*b* of strain sensor 540 to strain. The strain gauges 560*a*, 560*b* detect and measure the amount of this strain, such that an amount of stress imparted on strain sensor 540 can be calculated. The firing force of adapter assembly 200 is then calculated using the calculated amount of stress imparted on strain sensor 540.

As mentioned above, force transmitting assembly 520 is also configured to detect and measure retraction forces of adapter assembly 200. In operation, a force is applied, in a direction indicated by arrow "F" in FIG. 7, to drive shaft 522 and is transmitted distally along force transmitting assembly 520 to flange 526*a* of proximal portion 524*a* of drive shaft 522. Flange 526*a* of proximal portion 524*a* of drive shaft 522 transmits the force to strain sensor 540 through first bearing 530*a*. This force causes strain gauges 560*a*, 560*b* of strain sensor 540 to strain. Strain gauges 560*a*, 560*b* detect and measure the amount of strain they undergo, such that an amount of stress imparted on strain sensor 540 can be calculated. The retraction force of adapter assembly 200 is then calculated using the calculated amount of stress imparted on strain sensor 540.

Any of the components described herein may be fabricated from either metals, plastics, resins, composites or the like taking into consideration strength, durability, wearability, weight, resistance to corrosion, ease of manufacturing, cost of manufacturing, and the like.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. A force transmitting assembly of an adapter assembly, comprising:
    a rotatable drive shaft including:
        a proximal portion configured to be operatively coupled to a driving member of a handle assembly;
        a distal portion including a threaded portion; and
        a flange supported on and extending from the drive shaft;
    a proximal strain sensor coupled to the drive shaft and disposed adjacent the flange such that longitudinal movement of the drive shaft imparts a force on the proximal strain sensor via the flange;
    a distal strain sensor distally spaced from the proximal strain sensor, the flange being disposed between the proximal and distal strain sensors; and
    a distal drive member having a proximal end coupled to the threaded portion of the drive shaft and a distal end configured to be operatively coupled to a driven member of a surgical loading unit, wherein rotation of the drive shaft longitudinally moves the distal drive member relative to the drive shaft to actuate the surgical loading unit.

2. The force transmitting assembly according to claim 1, wherein the proximal strain sensor includes at least one strain gauge.

3. The force transmitting assembly according to claim 2, wherein the proximal strain sensor further includes:
    a plate disposed about the drive shaft; and
    a mounting member connected to the plate and defining a passage therethrough having the drive shaft received therein, the at least one strain gauge is disposed on the mounting member.

4. The force transmitting assembly according to claim 3, wherein the mounting member is fabricated from a resilient metal material.

5. The force transmitting assembly according to claim 3, wherein the at least one strain gauge includes a first set of strain gauges disposed on a proximally-oriented surface of the mounting member and a second set of strain gauges disposed on a distally-oriented surface of the mounting member.

6. The force transmitting assembly according to claim 1, wherein the drive shaft further includes a bearing disposed between the flange and the proximal strain sensor, the proximal portion of the drive shaft extending through the bearing.

7. The force transmitting assembly according to claim 1, wherein the drive shaft further includes a pair of bearings disposed between the proximal and distal strain sensors, the flange being disposed between the pair of bearings.

8. An adapter assembly for selectively interconnecting a surgical loading unit and a handle assembly that is configured to actuate the surgical loading unit, the adapter assembly comprising:
    a housing configured and adapted for selective connection with the handle assembly;
    an outer tube having a proximal end supported by the housing and a distal end configured to be coupled with the surgical loading unit, and
    a force transmitting assembly extending at least partially through the outer tube and including:
        a rotatable drive shaft including:
            a proximal portion configured to be operatively coupled to a rotatable driving member of the handle assembly;
            a distal portion including a threaded portion; and
            a flange supported on and extending from the drive shaft;
        a proximal strain sensor coupled to the drive shaft and affixed to the housing, the proximal strain sensor disposed adjacent the flange such that longitudinal movement of the drive shaft imparts a force on the proximal strain sensor via the flange;
        a distal strain sensor distally spaced from the proximal strain sensor, the flange being disposed between the proximal and distal strain sensors; and
        a distal drive member having a proximal end coupled to the threaded portion of the drive shaft and a distal end configured to be operatively coupled to a translatable driven member of the surgical loading unit, wherein rotation of the drive shaft longitudinally moves the distal drive member relative to the drive shaft to actuate the surgical loading unit.

9. The adapter assembly according to claim 8, wherein the proximal strain sensor includes at least one strain gauge.

10. The adapter assembly according to claim 9, wherein the proximal strain sensor further includes:
    a plate disposed about the drive shaft and affixed to the housing; and a mounting member connected to the plate and defining a passage therethrough having the drive shaft received therein, the at least one strain gauge disposed on the mounting member.

11. The adapter assembly according to claim 10, wherein the mounting member is fabricated from a resilient metal material.

12. The adapter assembly according to claim 10, wherein the at least one strain gauge includes a first set of strain gauges disposed on a proximally-oriented surface of the mounting member and a second set of strain gauges disposed on a distally-oriented surface of the mounting member.

13. The adapter assembly according to claim 8, wherein the drive shaft further includes a bearing disposed between the flange and the proximal strain sensor, the proximal portion of the drive shaft extending through the bearing.

14. The adapter assembly according to claim 8, wherein the drive shaft further includes a pair of bearings disposed between the proximal and distal strain sensors, the flange being disposed between the pair of bearings.

15. A surgical instrument, comprising:
a handle assembly including a rotatable driving member;
an adapter assembly including:
   a housing coupled with the handle assembly;
   an outer tube having a proximal end supported by the housing and a distal end; and
   a force transmitting assembly extending at least partially through the outer tube and including:
     a rotatable drive shaft including:
       a proximal portion operatively coupled to the rotatable driving member of the handle assembly; and
       a distal portion including a flange and a threaded portion;
     a proximal strain sensor coupled to the drive shaft and affixed to the housing, the proximal strain sensor disposed adjacent the flange such that longitudinal movement of the drive shaft imparts a force on the proximal strain sensor via the flange;
     a distal strain sensor distally spaced from the proximal strain sensor, the flange being disposed between the proximal and distal strain sensors; and
     a distal drive member having a proximal end coupled to the threaded portion of the drive shaft and a distal end; and
a surgical loading unit configured to be actuated by the handle assembly and including a translatable driven member operatively coupled to the distal end of the distal drive member of the force transmitting assembly, wherein rotation of the drive shaft longitudinally moves the distal drive member relative to the drive shaft to actuate the surgical loading unit.

16. The surgical instrument according to claim 15, wherein the proximal strain sensor includes at least one strain gauge.

* * * * *